United States Patent [19]
Weisbart

[11] Patent Number: 6,090,380
[45] Date of Patent: Jul. 18, 2000

[54] TREATMENT OF RHEUMATOID ARTHRITIS BY ORAL ADMINISTRATION OF POOLED HUMAN IMMUNOGLOBULIN

[75] Inventor: Richard Weisbart, Los Angeles, Calif.

[73] Assignee: Research Corporation Technologies, Inc., Tucson, Ariz.

[21] Appl. No.: 08/445,595

[22] Filed: May 22, 1995

Related U.S. Application Data

[63] Continuation of application No. 08/180,229, Jan. 12, 1994, abandoned.

[51] Int. Cl.$^7$ .................. A61K 39/395; C07K 16/00; C07K 16/06; C07K 16/44
[52] U.S. Cl. ................... 424/130.1; 424/176.1; 424/177.1; 424/810; 530/868; 530/386; 530/387.1; 530/389.1; 530/390.1; 530/390.5
[58] Field of Search ............... 424/130.1, 176.1, 424/177.1, 810; 530/868, 386, 387.1, 389.1, 390.1, 390.5

[56] References Cited

U.S. PATENT DOCUMENTS

| | | | |
|---|---|---|---|
| Re. 33,565 | 4/1991 | Stolle et al. | 424/157.1 |
| 4,477,432 | 10/1984 | Hardie | 424/165.1 |
| 5,242,691 | 9/1993 | Beck | 424/535 |
| 5,681,571 | 10/1997 | Holmgren et al. | 424/236.1 |

OTHER PUBLICATIONS

Silverman et al., J. Rheumatol., 21: 2353–2358, 1994 Alarcow, "Rheumatology and Immunology", Chapter 28, Second Edition, Harcourt Brace Jovanovich, 1986.
Silverman et al., Arth and Rheum, 33:1015–1022, 1990.
Edginston, Bio/Technology, 10: 383–386, 388, 389, 1992.
Herman et al., Annu. Rev. Immunol., 9:745–772 (1991).
Drake et al., J. Clin. Immunol., 12P149–162 (1992).
Takei et al., J. Clin. Invest., 91:602–607 (1993).
Rich, J. Clin. Invest., 91–378 (1993).
Sandoglobulin Brochure, (1991).
Trentham et al., Science, 261:1727 (1993).
Weiner et al., Science, 259:1321 (1993).
Palliard et al., Science, 253:325 (1991).

*Primary Examiner*—Ronald B. Schwadron
*Attorney, Agent, or Firm*—Scully, Scott, Murphy & Presser

[57] ABSTRACT

Pooled human immunoglobulin may be administered orally to rheumatoid arthritis patients to treat the rheumatoid arthritic condition of those patients. Oral administration of pooled human immunoglobulin can result in significant clinical improvement in the level of disease activity in patients with rheumatoid arthritis.

6 Claims, 7 Drawing Sheets

TREATMENT OF RHEUMATOID ARTHRITIS BY ORAL ADMINISTRATION OF POOLED HUMAN IMMUNOGLOBULIN

This is a continuation of Ser. No. 08/180,229 filed on Jan. 12, 1994 (now abandoned).

BACKGROUND OF THE INVENTION

1. Field of the Invention

The present invention relates generally to the treatment of rheumatoid arthritis. More particularly, the invention relates to the treatment of rheumatoid arthritis by oral administration of pooled human immunoglobulin.

2. Description of Related Art

The publications and other reference materials referred to herein to describe the background of the invention and to provide additional detail regarding its practice are hereby incorporated by reference.

Rheumatoid arthritis ("rheumatoid arthritis") is a systematic inflammatory disease that commonly affects the joints, particularly those of the hands and feet. The onset of rheumatoid arthritis can occur slowly, ranging from a few weeks to a few months, or the condition can surface rapidly in an acute manner.

Today, over 2,500,000 individuals are diagnosed with rheumatoid arthritis in the United States alone (1% of population), with some statistics indicating from 6.5 to 8 million potentially afflicted with the disease. Women are affected 2–3 times more often than men. The disease can occur at any age and typically will increase in incidence with age.

The classic early symptoms of rheumatoid arthritis include stiffness, tenderness, fever, subcutaneous nodules, achy joints, and fatigue. The joints of the hands, feet, knees and wrists are most commonly affected, with eventual involvement of the hips, elbows and shoulders. As the joints stiffen and swell, any type of motion becomes very painful and difficult. The more severe cases of rheumatoid arthritis can lead to intense pain and eventual joint destruction. Some 300,000 bone and joint replacement surgical procedures are performed annually in an effort to alleviate the pain and mobility loss resultant from arthritis related joint destruction.

The effective treatment of rheumatoid arthritis has generally comprised a combination of medication, exercise, rest and proper joint protection therapy. The therapy for a particular patient depends on the severity of the disease and the joints that are involved. Aspirin is widely used for pain and to reduce inflammation. In addition to aspirin, non-steroidal anti-inflammatory drugs, corti-costeroids, gold salts, anti-malarials and systemic immunosuppressants are widely used in moderate to advanced cases. The use of steroids and immunosuppressants, however, has significant risks and side effects both in terms of toxicity and vulnerability to potentially lethal conditions. There, thus exists a need for a method of treating rheumatoid arthritis which does not entail the potentially lethal side effects associated with the treatments described above.

"Superantigens" have been considered as stimulants of the immune system in various autoimmune diseases including rheumatoid arthritis. Herman, A., et al. (1991) *Annu. Rev. Immunol.* 9:745–772; Drake, C. G. and Kotzin, B. L. (1992) *J. Clin. Immunol.* 12:149–162. The gastrointestinal tract may be the site of immunologic stimulation by superantigens. There may be a defect in the ability of patients with rheumatoid arthritis to produce antibodies with the correct neutralizing specificities. One approach to treating rheumatoid arthritis is to orally administer cow's milk to patients. See U.S. Pat. No. 4,732,757 (Stolle et al.). Therein it is disclosed that rheumatoid arthritis may be treated by the oral administration of cow's milk, the milk containing IgGs against a large group of bacteria with which the producing cow was vaccinated. The drawbacks to this approach are twofold. First, some patients have adverse reactions to consumption of bovine milk; second, cow's milk does not contain the entire spectrum of antibodies present in a human.

A second approach to the treatment of autoimmune diseases, of which rheumatoid arthritis is an example, is tolerazation of the patient suffering from the autoimmune disease to the particular autoantigen(s) involved in the disease. In Weiner et al., *Science* 259:1321–1324 (1993), multiple sclerosis patients were orally administered bovine myelin protein, which contains two of the diseases autoantigens. In Trentham et al., *Science* 261:1727–1730 (1993), rheumatoid arthritis patients were orally administered collagen, a presumed autoantigen. The drawback to tolerazation is identification of the correct autoantigen to which tolerance is to be induced.

In view of the above there is a continued need to develop methods for the treatment of rheumatoid arthritis.

SUMMARY OF THE INVENTION

In accordance with the present invention, a method is provided for treating a rheumatoid arthritis patient comprising the step of orally administering to said patient an amount of pooled human immunoglobulin which is sufficient to provide a clinically observable improvement in said patient's rheumatoid arthritic condition. The present invention is based on the discovery that the oral administration of pooled human immunoglobulin to patients with rheumatoid arthritis can result in a significant clinical improvement in the rheumatoid arthritic condition of the patient. The present invention is further based on the discovery that there are no toxic effects of administering pooled human immunoglobulin to rheumatoid arthritis patients.

DESCRIPTION OF THE PREFERRED EMBODIMENTS

Figure 1:
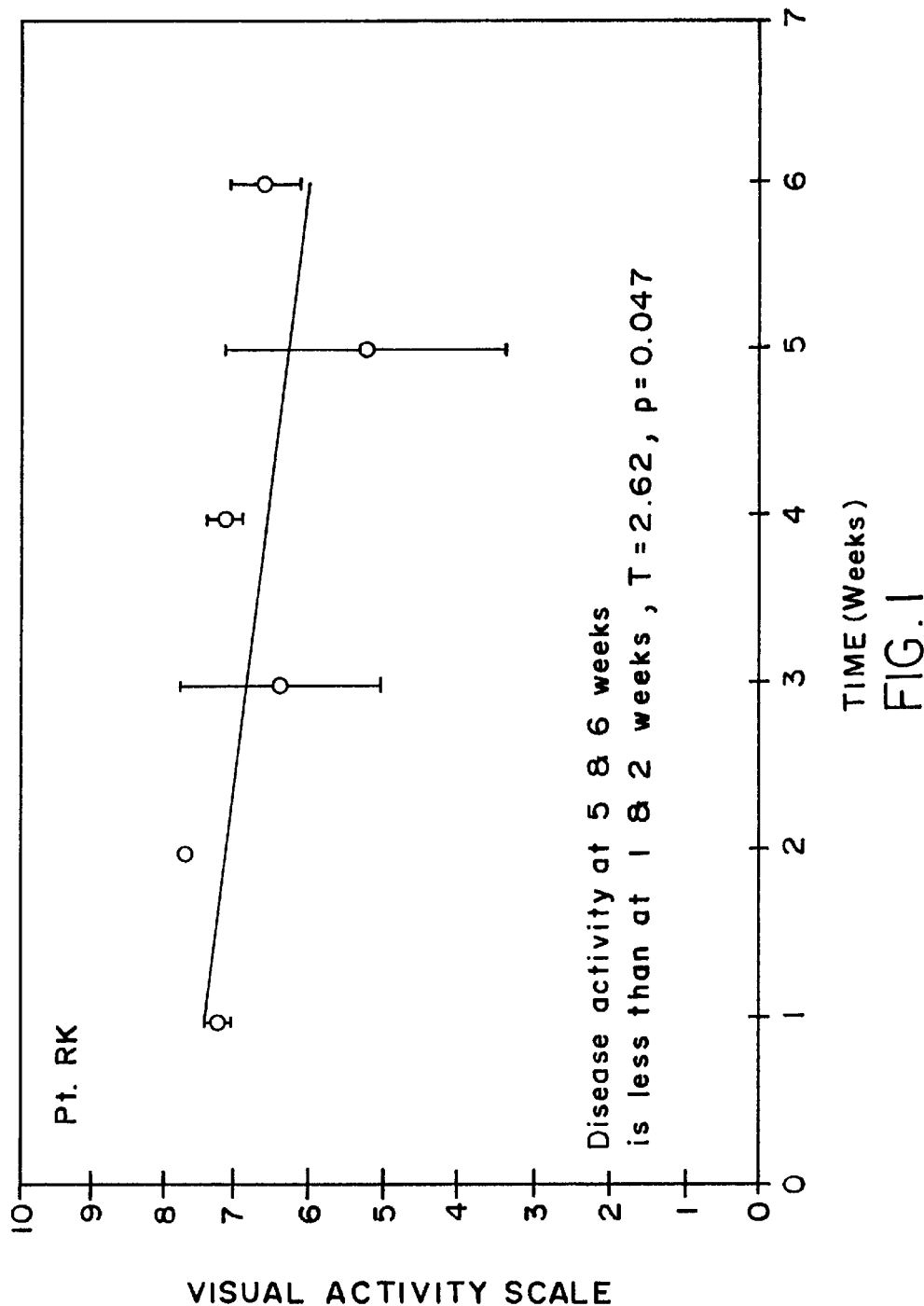
FIG. 1 is a Visual Activity plot for patient RK, who was treated in accord with the present invention.

The present invention concerns a method for treating a patient with rheumatoid arthritis. This is accomplished by orally administering pooled human immunoglobulin. It was discovered that the oral administration of pooled human immunoglobulin to rheumatoid arthritis patients could result in a significant clinical improvement in said patients. Further, it was discovered that oral administration of pooled human immunoglobulin resulted in no toxic side effects.

The term "pooled human immunoglobulin" as used with respect to the present invention is herein defined as a composition of immunoglobulins of whatever type, e.g. IgG, IgM, IgA, etc., or fragments thereof derived from human plasma, which composition is essentially free of non-immunoglobulin material. Preferably, the pooled human immunoglobulin is produced by cold alcohol fractionation from the plasma of multiples human volunteers. Most preferably, pooled human immunoglobulin is purchased from the Sandoz Pharmaceuticals Corporation, where it is sold under the name Immune Globulin Intravenous (Human) SANDOGLOBULIN®. SANDOGLOBULIN® pooled human immunoglobulin "is a sterile, highly purified polyvalent antibody product containing in concentrated form all the IgG antibodies which regularly occur in the donor population (1) [Gardi A: Quality control in the production of an immunoglobulin for intravenous use. *Blut* 48:337–344, 1984]. This immunoglobulin preparation is produced by cold alcohol fractionation from the plasma of over 16,000 volunteer US donors. * * * Sandoglobulin® (IGIV) is made suitable for intravenous use by treatment at acid pH in the presence of trace amounts of pepsin (2,3) [Römer J, Morgenthaler J J, Scherz R. et al: Characterization of various immunoglobulin preparations for intravenous application. I. Protein composition and antibody content. *Vox Sang* 42:74–80, 1982; Römer J, Späth P J, Skvaril G, et al: Characterization of various immunoglobulin preparations for intravenous application. III. Complement activation and binding to Staphylococcus protein A. *Vox Sang* 42:74–80, 1982.] The preparation contains at least 96% of IgG and with a neutral unbuffered diluent has a pH of 6.6±0.2. Most of the immunoglobulins are monomeric (7 S) IgG; the remainder consists of dimeric IgG and a small amount of polymeric IgG, traces of IgA and IgM and immunoglobulin fragments (4) [Römer J, Späth P J: Molecular composition of immunoglobulin preparations and its relation to complement activation, in Nydegger U E (ed): *Immunohemotherapy: A Guide to Immunoglobulin Prophylaxis and Therapy.* London, Academic Press, 1981, p. 123.]. The distribution of the IgG subclasses corresponds to that of normal serum (5,6,7,8) [Skvaril G, Roth-Wicky B, and Barandum S: IgG subclasses in human-γ-globulin preparations for intravenous use and their reactivity with Staphylococcus protein A. *Vox Sang* 38:147, 1980; Skvaril G: Qualitative and quantitative aspects of IgG subclasses in i.v. immunoglobulin preparations, in Nydegger U E (ed): *Immunohemotherapy: A Guide to Immunoglobulin Prophylaxis and Therapy.* London, Academic Press, 1981, p 113; Skvaril F, and Barandun S: In vitro characterization of immunoglobulins for intravenous use, in Alving B M, Finlayson J S (eds): *Immunoglobulins: Characteristics and Uses of Intravenous Preparations*, DHHS Publication No. (FDA)-80-9005. US Government Printing Office, 1980, pp 201–206; Burckhardt J J, Fardi A, Oxelius V, et al: Immunoglobulin G subclass distribution in three human intravenous immunoglobulin preparations. *Vox Sang* 57:10–14, 1989.]. Final container lyophilized units are prepared so as to contain 1, 3 or 6 g protein with 1.67 g sucrose and less than 20 mg NaCl per gram of protein. The lyophilized preparation is devoid of any preservatives and may be reconstituted with sterile water . . . ." ©1991, Sandoz Pharmaceutical Corporation.

In order to reduce the degree of inactivation of the introduced immunoglobulin in the stomach of the treated patient, it is preferred that an antiacid be administered simultaneously with the immunoglobulin. An immunoglobulin, introduced into the acidic environment of the human stomach, may suffer inactivation. To alleviate such inactivation, the pooled human immunoglobulin employed in the method of the present invention may be administered in conjunction with an antiacid, which neutralizes the otherwise acidic character of the gut. Preferably, the antiacid is aluminum hydroxide or magnesium hydroxide such as MAALOX antacid or MYLANTA antacid, which are available commercially. Most preferably the antiacid is an H2 blocker, such as Cimetidine or Ranitidine.

The dosage of antiacid administered in conjunction with immunoglobulin depends on the particular one used. When the antiacid is MYLANTA antacid, between 15 ml and 30 ml is preferred. Most preferably the dosage of MYLANTA antacid is 15 ml. When the cimetidine H2 blocker is used, the preferred dosage is between 400 and 800 mg per day.

The dosage of pooled human immunoglobulin administered to the patient may be varied depending upon severity of the patient's arthritic condition and other clinical facts. Preferably, the dosage will be as small as possible while still providing a clinically observable result. The most preferable doses are those that have the largest effect in terms of alleviating the patient's arthritic condition. Dosages may range from as little as 100 mg per day up to as much as 10 g per day. Dosages of 1000 mg of pooled human immunoglobulin per day have been found to result in significant improvement in the condition of patients with rheumatoid arthritis and cause little or no adverse side effects. Accordingly, 1000 mg per day is a preferred dose.

Although the chosen dosage may be given in increments, it also maybe given as a single dose. Further, although the dose of immunoglobulin may be administered at any time during the day, it is preferred that it be administered in the morning, prior to substantial patient activity.

The patient's arthritic condition can be determined for example by the patient's self-assessment of his or her pain, stiffness, etc. Another way to determine the patient's arthritic condition is for a physician to examine a patient's joint tenderness and swelling.

The pooled human immunoglobulin may be administered in any form that is suitable for oral ingestion. Preferably, however, it is administered in capsules containing powdered immunoglobulin. It is also preferred to administer the pooled human immunoglobulin dispersed in a pharmaceutically acceptable solution such as distilled water, saline or dextrose. Most preferably, 250 mg of dry lyophilized pooled human immunoglobulin is administered in standard gelatin capsules which are commercially available.

Clinically observable results from the administration of immunoglobulin may be observed in as little as 2 weeks. However, it may take up to 6 weeks to obtain measurable benefit. Initial dose levels used during the first few weeks of treatment may be reduced once clinical improvement has been observed. Reductions in dose levels of up to 99% may be made after the first few weeks.

The oral treatment method in accordance with the present invention may be used to treat rheumatoid arthritis and other closely related autoimmune diseases such as ankylosing spondylitis. The treatment of ankylosing spondylitis according to the present invention would employ the same dosages as for rheumatoid arthritis and the same treatment protocol.

Examples of the treatment of patients in accordance with the present invention are set forth in the following example.

EXAMPLES

Patients were selected who had severe, unrelenting disease unresponsive to conventional medications including corti-costeroids, methotrexate, and Imuran. These patients were extremely unlikely to have spontaneous remissions and were unlikely to receive a placebo effect. Each patient was administered 1 gram of pooled human immunoglobulin, purchased from Sandoz, orally each day for 6 weeks. The immunoglobulin was administered in four gelatin capsules each containing 250 mg of immunoglobulin.

Figure 2:
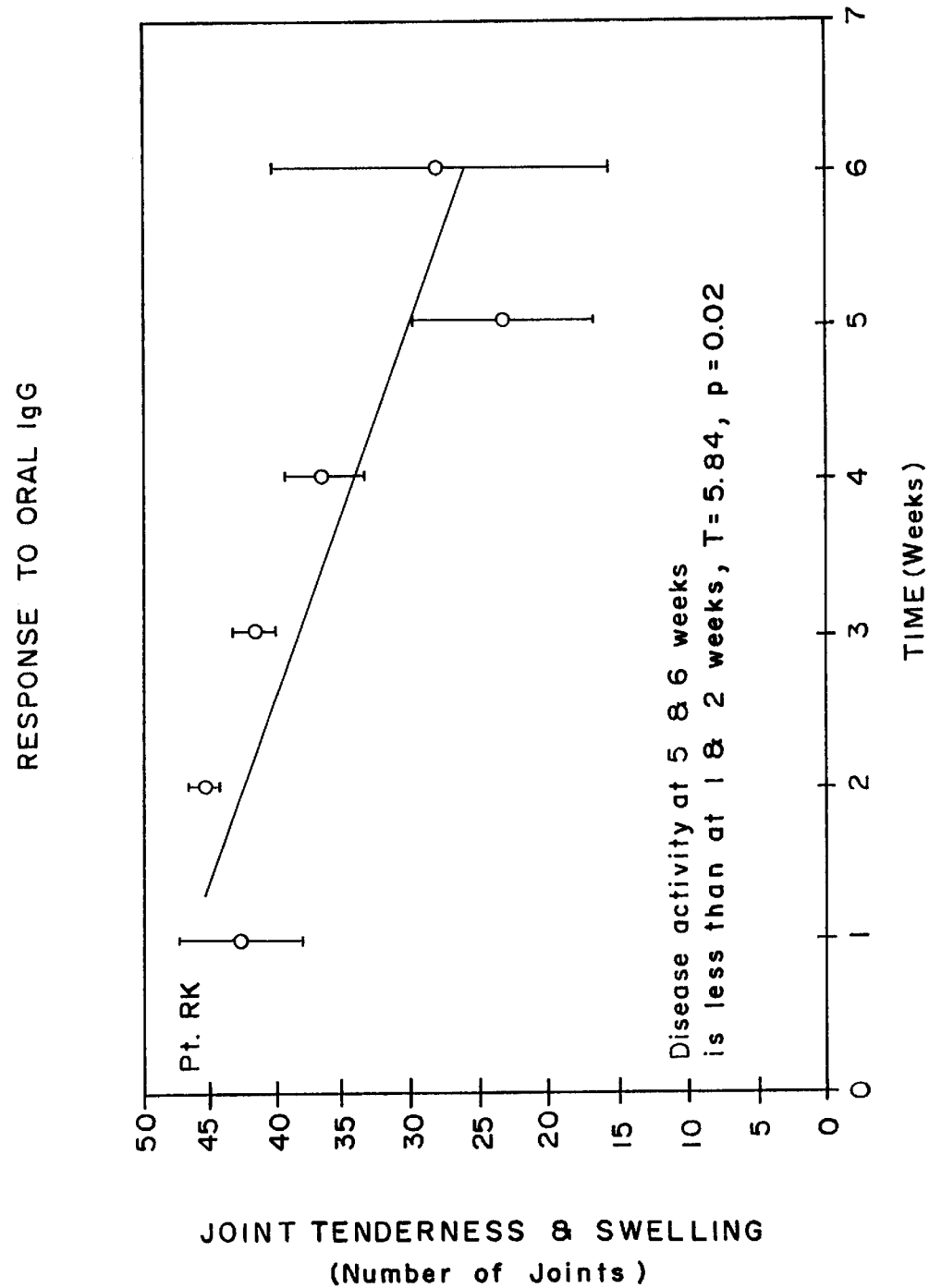
FIG. 2 is a Joint Tenderness & Swelling plot for patient RK (of FIG. 1, above).
Figure 3:
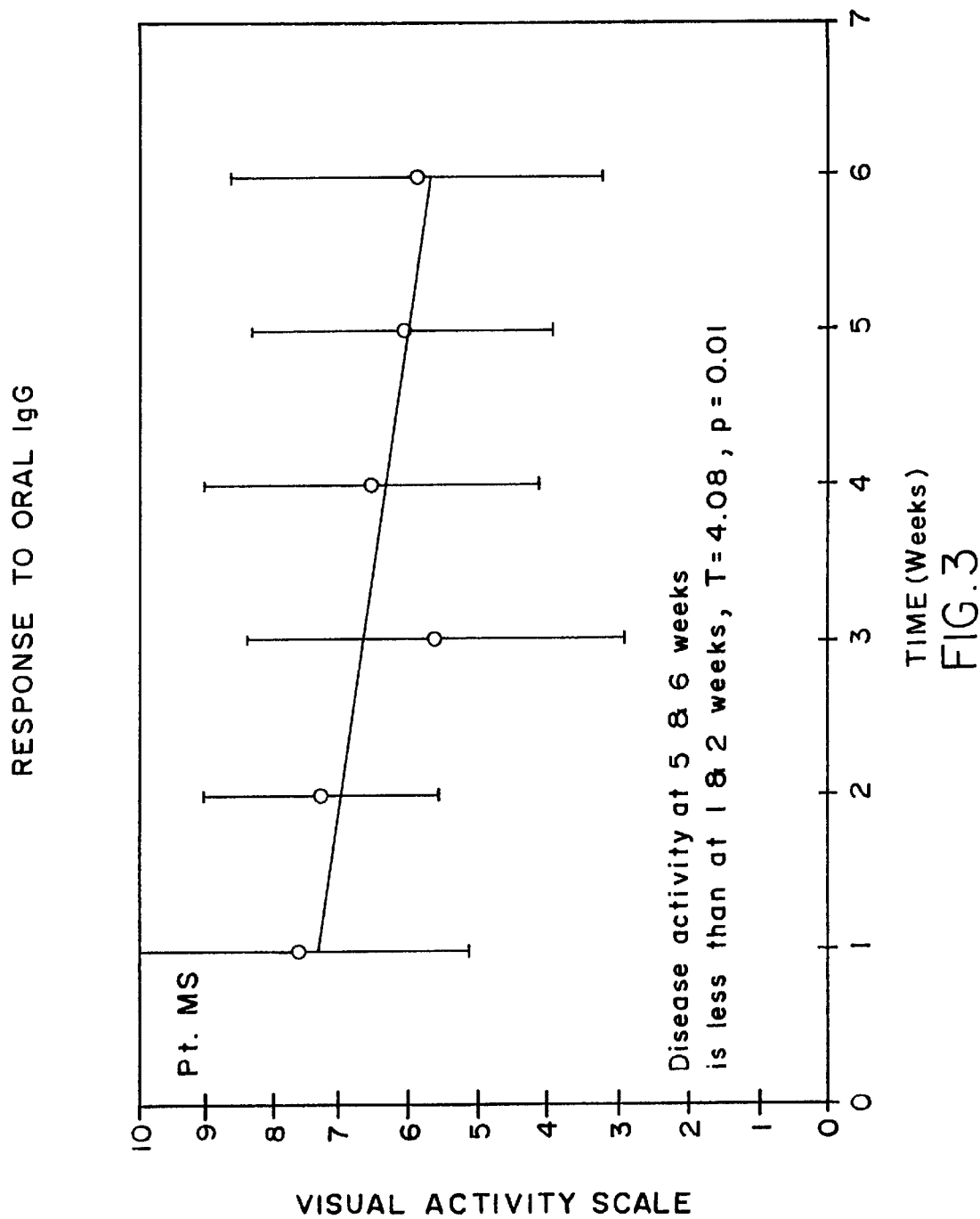
FIG. 3 is a Visual Activity plot for patient MS, who was treated in accord with the present invention.
Figure 4:
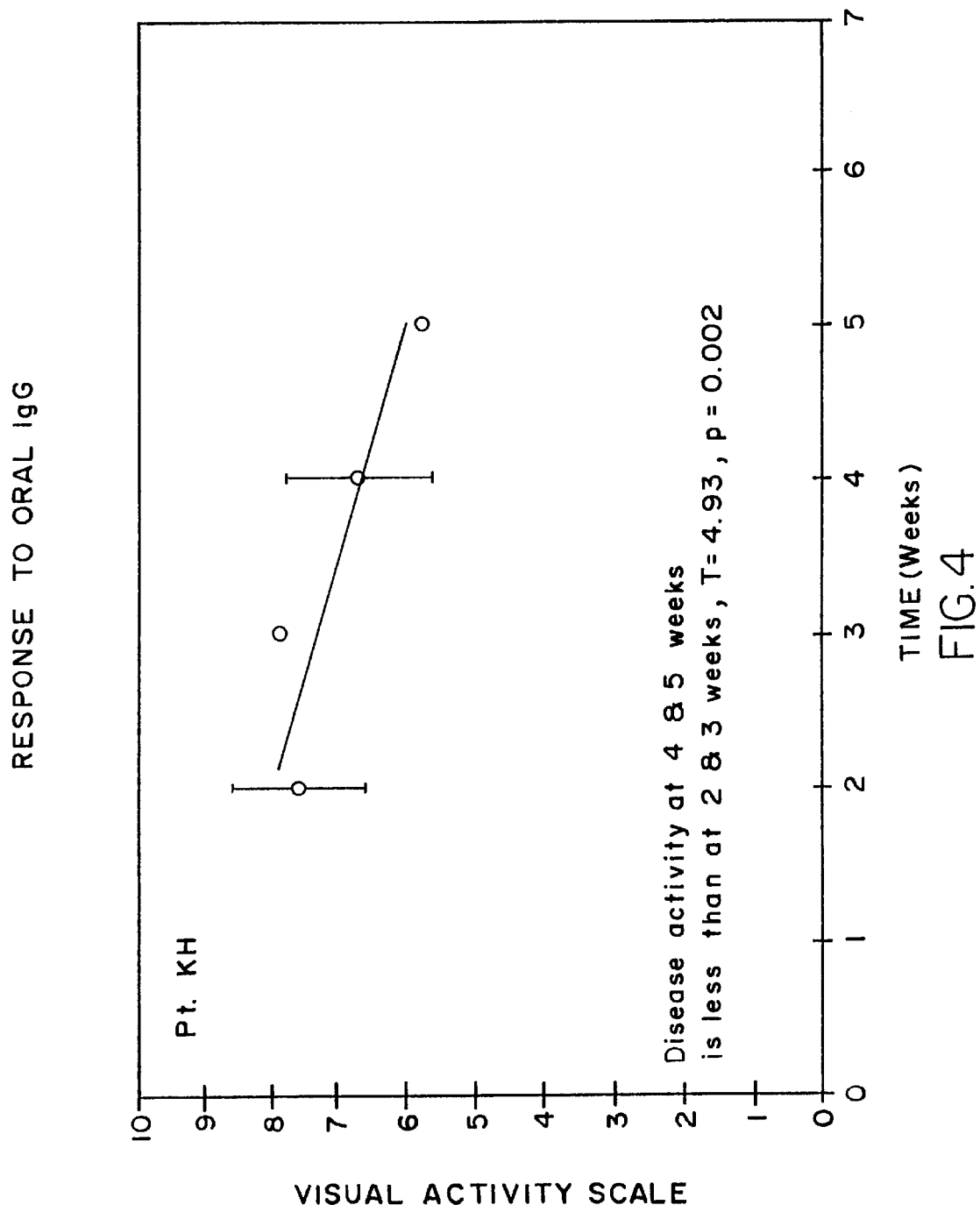
FIG. 4 is a Visual Activity plot for patient KH, who was treated in accord with the present invention.
Figure 5:
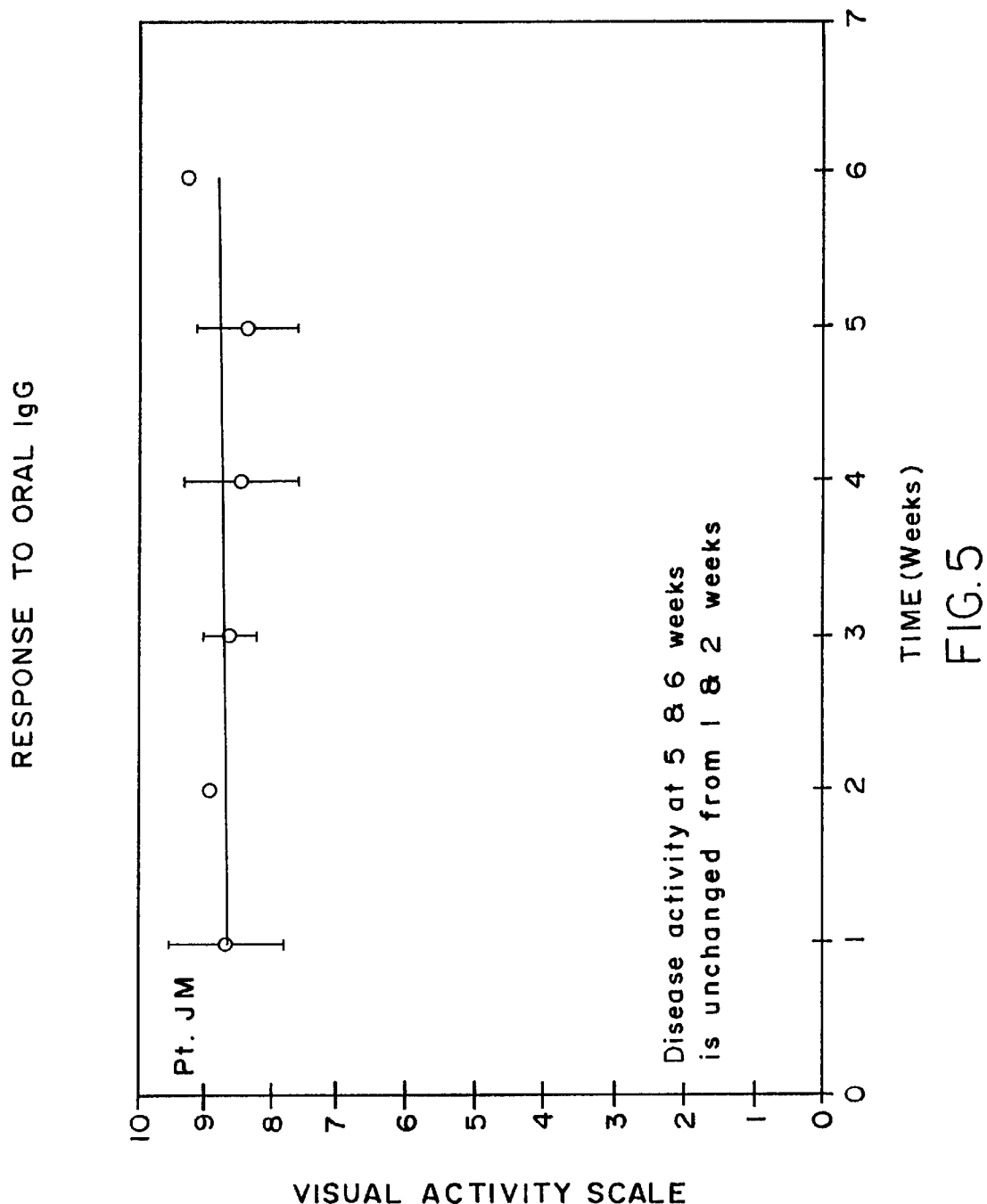
FIG. 5 is a Visual Activity plot for patient JM, who was treated in accord with the present invention.
Figure 6:
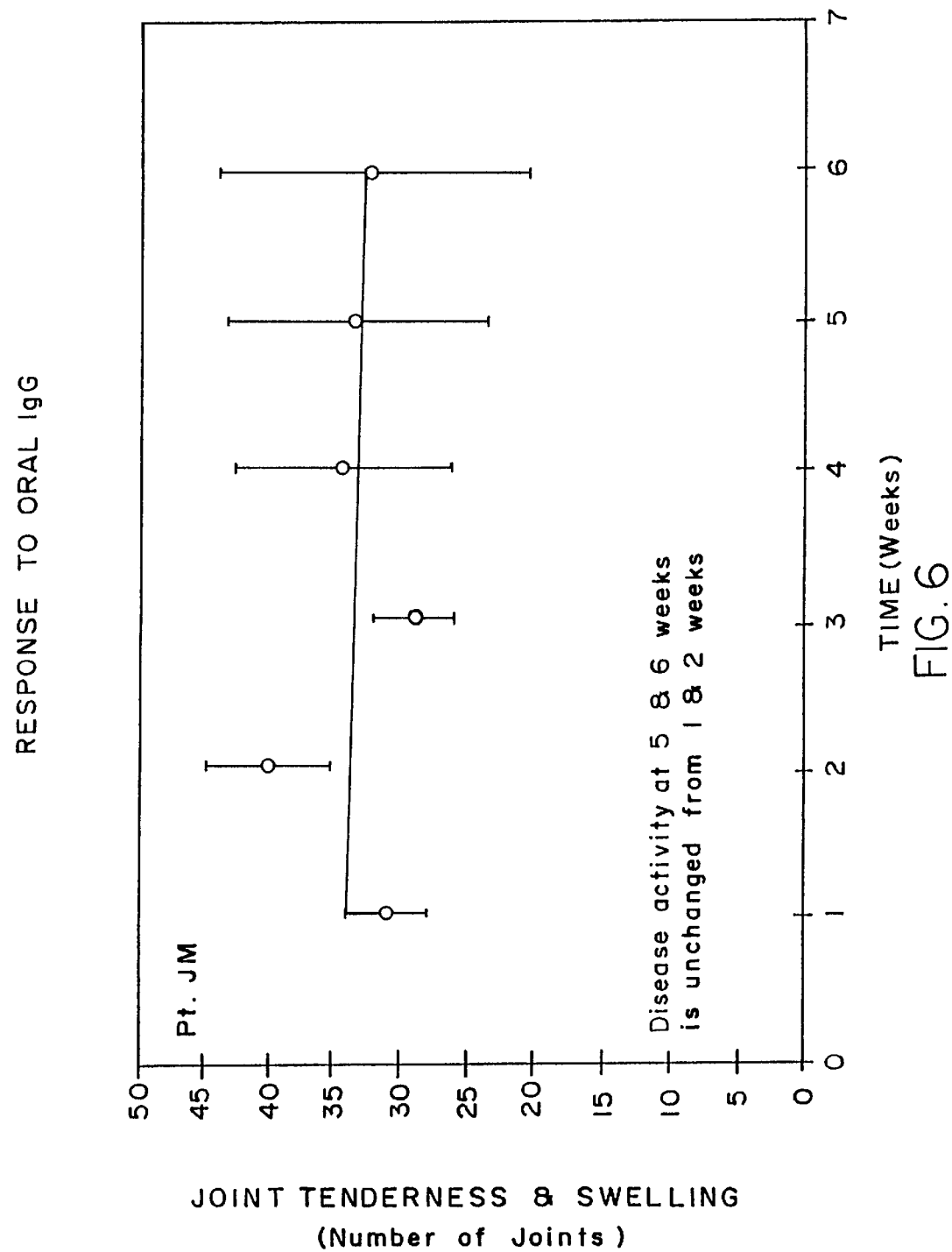
FIG. 6 is a Joint Tenderness and Swelling plot for patient JM (of FIG. 5, above).
Figure 7:
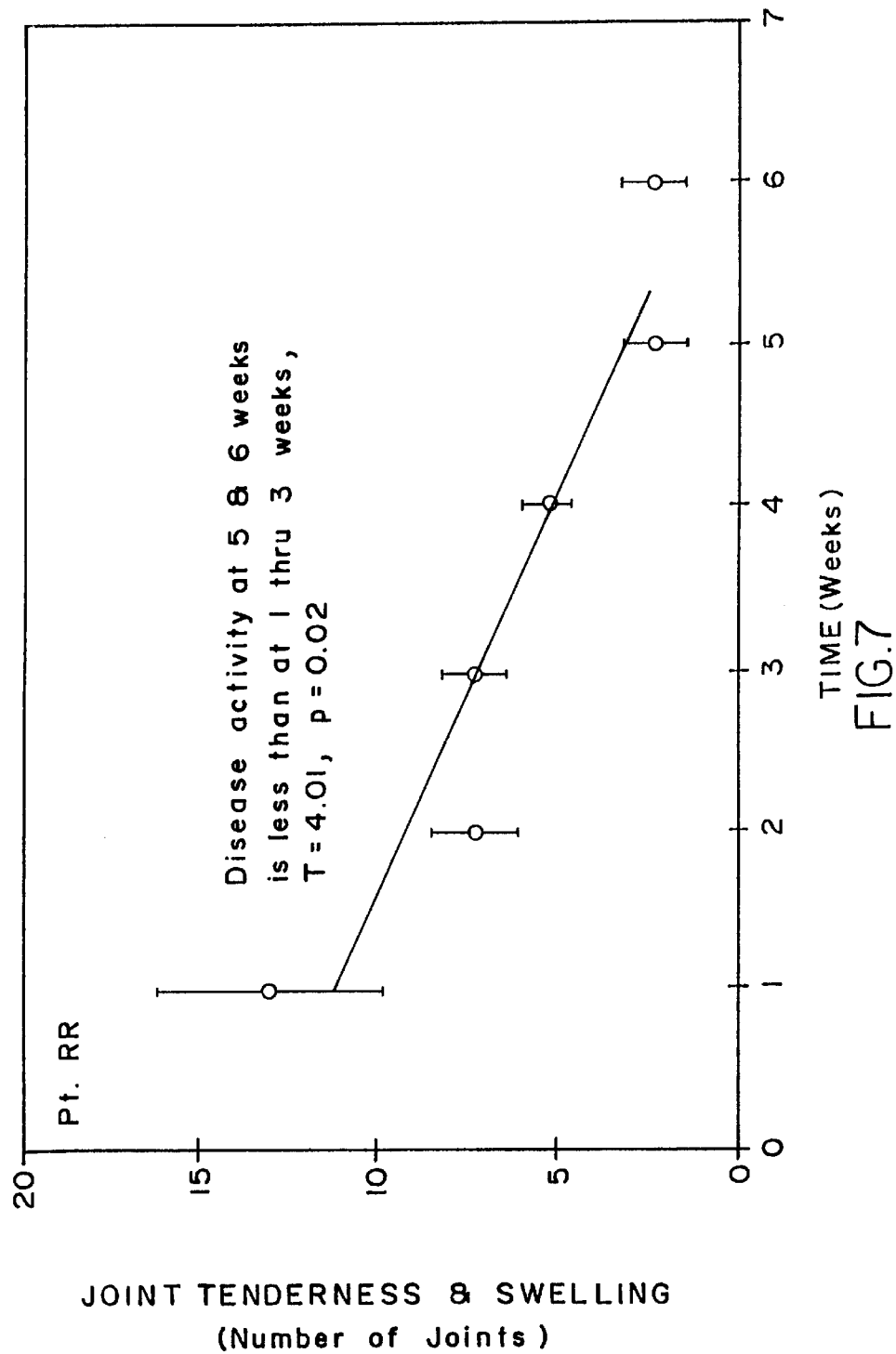
FIG. 7 is a Joint Tenderness and Swelling plot for patient RR who was treated in accord with the present invention.

An open study was done and the patients were monitored for response to therapy, either by Visual Activity, which is the patients own observations about his or her condition, or by Joint Tenderness and Swelling, which is measured by an examining physician. Significant clinical improvement was observed in four of the five patients (See FIGS. 1–7). Patient RK was treated as described above and his condition was observed for a period of six weeks. By both Visual Activity and Joint Tenderness & Swelling (FIGS. 1 & 2), patient RK's disease activity was less at weeks 5 and 6 than at weeks 1 and 2. Patient MS was treated as described above and his condition observed for a six week period. By Visual Activity (FIG. 3), patient MS's disease activity at weeks 5 and 6 was less than at weeks 1 and 2. Patient KH was treated as described above and his condition observed for a four week period. By Visual Activity (FIG. 4), patient KH's disease activity at weeks 4 and 5 was less than at weeks 2 and 3. Patient RR was treated as described above and his condition observed for a six week period. By Joint Tenderness and Swelling (FIG. 7), patient RR's disease activity was less at weeks 5 and 6 than at weeks 1 through 3. Patient JM was treated as described above and his condition observed for a period of 6 weeks. By both Visual Activity and Joint Tenderness and Swelling (FIGS. 5 & 6), patient JM's disease activity at weeks 5 and 6 was unchanged from weeks 1 and 2. The results obtained with patient JM are believed to result from the fact that patient JM suffers from an atypical clinical disease which is completely resistant to all conventional therapy. No evidence of toxicity from the administration of pooled human immunoglobulin was observed.

Having thus described exemplary embodiments of the present invention, it should be noted by those skilled in the art that the within disclosures are exemplary only and that various other alternatives, adaptions and modifications may be made within the scope of the present invention. Accordingly, the present invention is not limited to the specific embodiments as illustrated herein, but is only limited by the following claims.

What is claimed is:

1. A method of treating adult autoimmune rheumatoid arthritis in a patient comprising orally administering to said patient an immunoglobulin composition consisting essentially of pooled human polyclonal IgG antibodies in an amount sufficient to provide a clinically observable improvement in the rheumatoid arthritis of said patient.

2. The method according to claim 1 wherein the amount of said immunoglobulin composition which is administered to said patient is about 1,000 mg per day.

3. The method according to claim 1 wherein said composition is in a powdered form.

4. The method according to claim 1 wherein said composition is dispersed in a pharmaceutically acceptable solution.

5. The method according to claim 1 further comprising administering an antacid compound in conjunction with administration of said composition.

6. The method according to claim 5 wherein said composition is dispersed in a pharmaceutically acceptable solution.

* * * * *